United States Patent [19]

Ichikawa

[11] Patent Number: 5,645,773

[45] Date of Patent: Jul. 8, 1997

[54] METHOD FOR PLACING CONCRETE FOR CONSTRUCTION OF A MASTER CONCRETE STRUCTURE

[75] Inventor: Yasuaki Ichikawa, Nagoya, Japan

[73] Assignee: E.R.C. Co., Ltd., Nagoya, Japan

[21] Appl. No.: 483,416

[22] Filed: Jun. 7, 1995

[30] Foreign Application Priority Data

Nov. 30, 1994 [CN] China ................................. 94112848.2

[51] Int. Cl.$^6$ ........................................................ E04B 1/16

[52] U.S. Cl. .............................. 264/31; 264/33; 264/34; 264/40.6; 264/327; 264/333

[58] Field of Search ........................... 264/31–35, 234, 264/237, 345, 348, 333, 40.1, 40.6, 327

[56] References Cited

FOREIGN PATENT DOCUMENTS 6-193033   7/1994   Japan .
7-119299   5/1995   Japan .

OTHER PUBLICATIONS

T. Hirose et al., Dam Technology No. 28 published 1988, pp. 15–23, "Method for Designing Temperature Control in RCD Method" (with English summary).

M. Strauss, et al., Bureau of Reclamation, U.S. Department of the Interior, published 1949, "Cooling of Concrete Dams".

*Primary Examiner*—Karen Aftergut
*Attorney, Agent, or Firm*—Lowe, Price, LeBlanc & Becker

[57] ABSTRACT

A method for placing concrete on a rock foundation to construct a massive concrete structure, such as a dam, a bridge pier or a foundation of a building, precludes development of cracks in the concrete by thermal stress. According to the method, stress exceeding an allowable limit for crack initiation and propagation is controlled by the following steps: (a) determining a temperature influence function to enable calculation of a thermal stress distribution under a temperature change by using results of a numerical analysis; (b) identifying a portion of the structure at which a crack will develop, by using said temperature influence function and a function of thermal change in said structure; (c) partially heating/cooling the vicinity of the identified portion and redistributing the excess stress predicted to cause cracking in the structure; and (d) reducing thermal stress in the structure by transmitting excess heat generated in the structure to another portion of the structure, at a location at which crack development is not predicted. Preferably, a heat pump system is used for transferring the excess generated heat to another portion of the structure to control the excess stress.

4 Claims, 6 Drawing Sheets

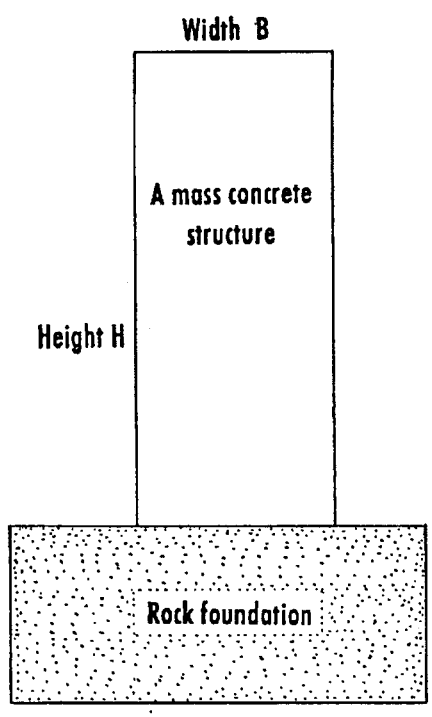
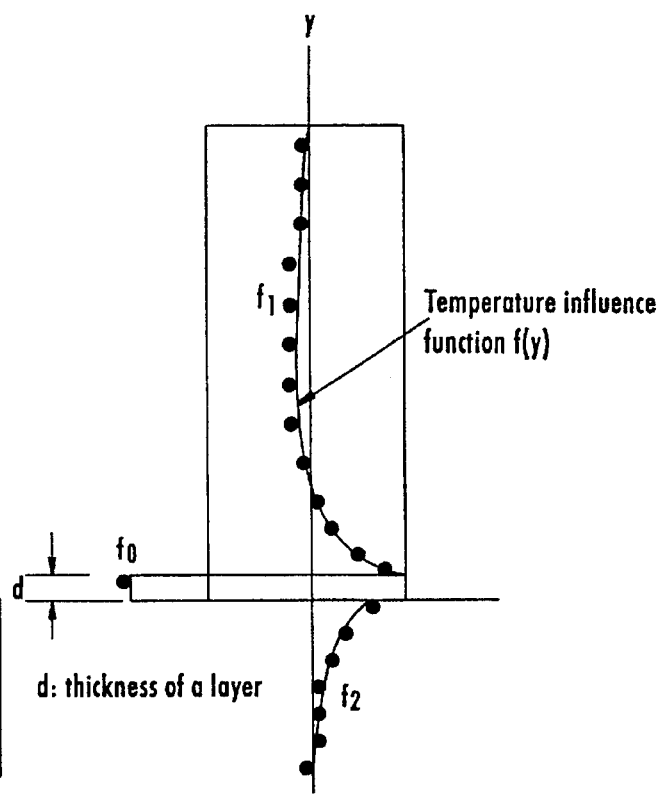
Figure 2(a)
Figure 2(b)

Figure 3 (unit: ×10⁻² ff/m²)

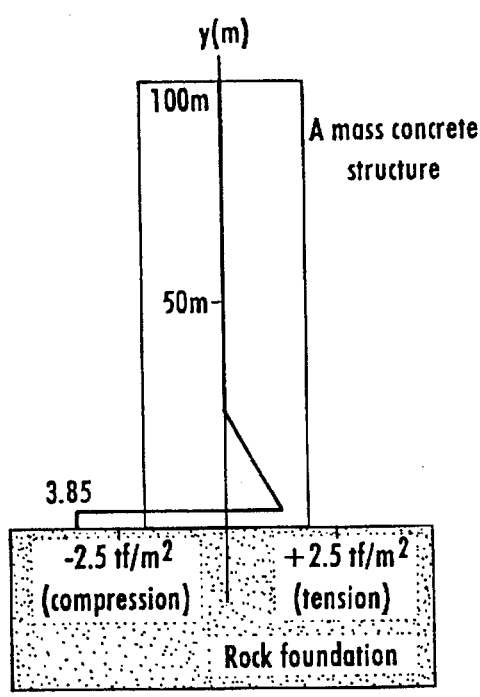
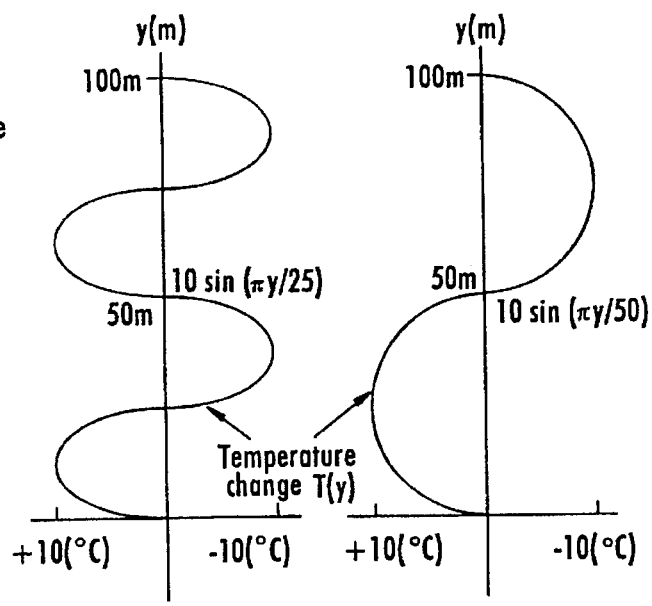
Figure 4(a)    Figure 4(b)    Figure 4(c)

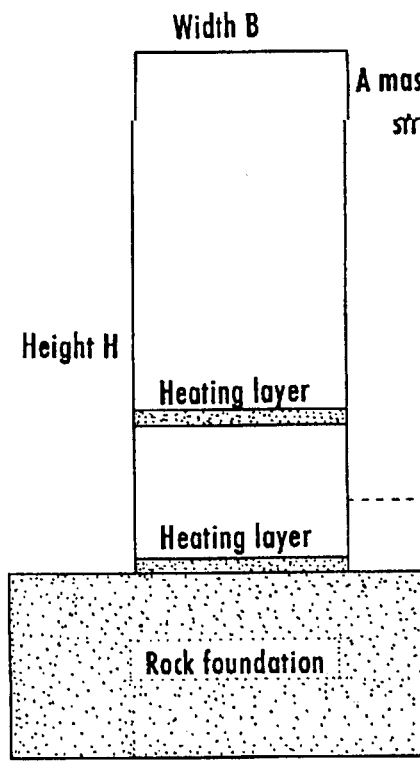
Figure 5(a) Heating layers
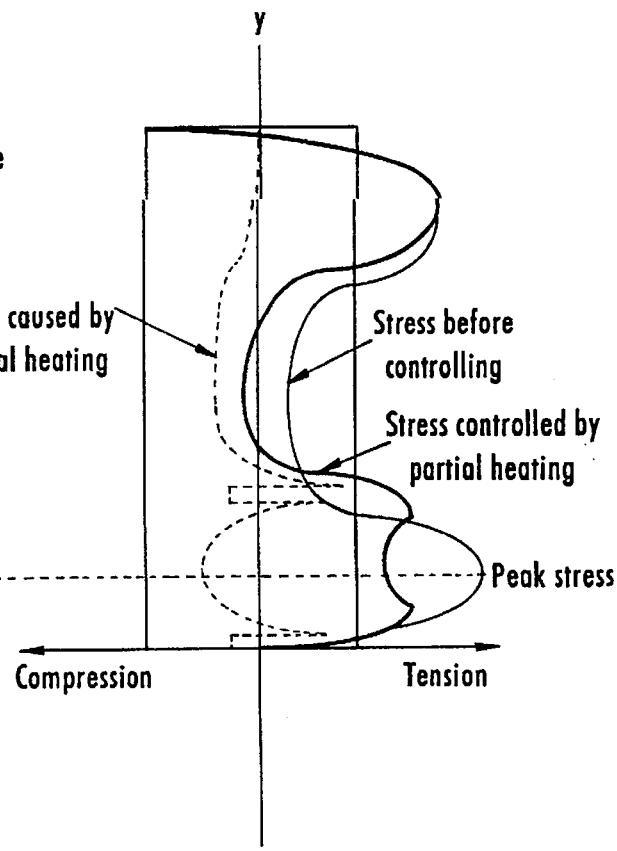
Figure 5(b) Stress distributions
Pattern for heating at $t=t_1$
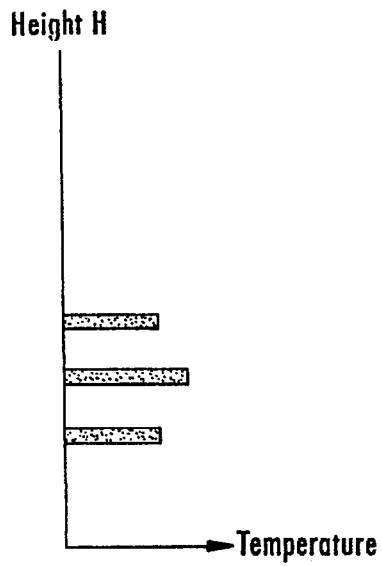
Pattern for heating at $t=t_2$
Figure 5(c) Patterns for heating

METHOD FOR PLACING CONCRETE FOR CONSTRUCTION OF A MASTER CONCRETE STRUCTURE

FIELD OF THE INVENTION

This invention relates to a method for placing concrete to construct a massive concrete structure such as a dam, a bridge pier or a foundation of a building, and more particularly to a method for placing concrete which prevents formation of cracks in the concrete.

BACKGROUND OF THE INVENTION

When designing and constructing a massive concrete structure, such as a concrete dam, a foundation for a main tower or an anchorage for a suspension bridge, a major concern relates to a rise in temperature of the structure.

Temperature variation of the structure is caused by a combined effect of (a) heat generation by hydration of cement and (b) seasonal and daily change in temperature of the atmospheric air. In particular, during construction of such a structure, hydrating heat may cause a temperature rise of about 15° to 25° Celsius. Most of the stresses to which the concrete structure under construction is subjected during such a temperature rise are compressive stresses. However, because the concrete is still young, the levels of these compressive stresses are negligibly small and, therefore, the modulus of elasticity is also small and the concrete shows creep behavior.

After reaching its peak temperature, the concrete structure starts to cool down. Since the concrete has developed reasonable elastic properties by that time, a high level of tensile stress is observed in the concrete due both to a constraint by a rock foundation (which is called a "foundation constraint effect" or an "external constraint effect") and to a constraint by the concrete itself (which is called an "internal constraint effect"). On the other hand, the temperature of the underlying concrete is equal to the atmospheric temperature and, therefore, the temperature distribution of a completed large-size concrete structure exhibits a periodic profile in its vertical direction, because of the long time required to complete such a large-sized structure, and because the atmospheric temperature naturally varies periodically during construction of the structure.

For example, yearly variation of air temperature in Japan is ±12° Celsius, or more. This periodic temperature change, coupled with a reduction in temperature due to the hydration heat after the concrete structure has reached its peak temperature, may produce cracks in the massive concrete structure. Once a crack develops in the concrete, it may propagate suddenly or cause additional cracks, thus causing great damage to the structure.

Accordingly, several techniques have been developed and used for controlling the temperature of a massive concrete structure or for preventing crack initiation and propagation therein. Any such a technique must be applied with due consideration of the size, type, period and method of construction of the structure, the duration of the construction, the thermal properties of the concrete used therein, and the weather conditions at the construction site. In particular, one or more of the following techniques are typically utilized:

(1) Where the amount of heat which will be generated and stored in the placed concrete is estimated correctly, an adequate construction method may be used for suppressing the temperature rise as much as possible. For example, one may reduce the quantity of cement used, may place concrete in half lifts, or may use a pipe cooling or pre-cooling technology.

(2) A contraction joint may be provided in advance, at locations where cracks are projected to develop.

(3) A proper design or construction procedure may be used to prevent crack initiation in the concrete. For example, the concrete layer adjacent the rock foundation, which will be strongly constrained by the rock, may be placed in a season having relatively lower temperatures. Moreover, the placed layer of concrete, when still at a height level lower than the final design height, should not be exposed for a long time. Further, the surface of the placed concrete should be adiabatically cured to prevent a rapid temperature change. Furthermore, the concrete can be placed with appropriate consideration of its creep characteristics.

The foregoing techniques must be used selectively in order to prevent crack initiation and propagation. Accordingly, it is very important to determine correctly the temperature distribution occurring during and after construction of the massive concrete structure.

In that regard, various methods have been proposed to determine temperature distributions and the thermal stresses corresponding thereto. It is a common recent practice to apply a numerical analysis, such as a finite element or boundary element method, which takes into consideration heat generation by hydration and a nonlinear behavior due to concrete hardening. However, a conventional design method, using a concept of constraint factor, continues to be in common use for determining a stress vertical distribution. In particular, this method is widely used for outline design of the concrete structure because, in such design, numerous design cases must be examined.

Stress may be estimated by using the concept of constraint factor, as follows: Let R be a constraint factor of a rectangular concrete block placed on a rock foundation. Stress is determined as a function of the geometry and material properties of both of the massive concrete structure and of the rock foundation. The factor is typically given in the form of a graph or a chart. Then, the horizontal stress $\sigma$ is calculated as $$\sigma = R\, E_c\, \alpha_c\, \Delta T,$$

where $E_c$ is the elastic modulus of concrete, $\alpha_c$ the thermal expansion coefficient of concrete, and $\Delta T$ the temperature change, which has typically been estimated as $\Delta T = T_r + Ta - Tm$, where $T_r$ is a reduction in the concrete temperature after the peak temperature, $T_m$ the mean air temperature and Ta is the amplitude of seasonal change of the mean air temperature.

This procedure for stress estimation is based on an assumption that a rectangular-shaped concrete block is placed on a semi-infinite layer, and that a uniform temperature drop $\Delta T$ will occur in the block. Therefore, with this procedure it is impossible to calculate the stress that will occur in each layer formed under an atmospheric temperature which changes from season to season.

In view of the difficulties of the prior art, it is thus important to establish a simple and accurate method for analyzing the stress that will occur in each of the concrete layers due to variations in the atmospheric temperature. Such a method can then be used to develop an optimal method for designing a desired concrete structure and determining an appropriately corresponding construction sequence.

It is further noted that conventional cooling procedures such as pipe cooling and pre-cooling, which intend to keep the concrete temperature under a certain level in order to prevent cracks from developing in concrete, are not efficient. Pipe cooling, which uses water pipes to remove heat, is not cost-effective because of the necessity to cool all the concrete layers uniformly. Such uniform cooling requires a large-scale cooling apparatus. Pre-cooling, which forces cooling down of concrete materials before mixing, makes it difficult to control the concrete temperature before placing because the concrete materials become warmed during transportation to the construction site, so that pre-cooling also is not cost-efficient.

It is accordingly an object of the invention to overcome the difficulties of the prior art and to provide a novel method for placing concrete in design and construction of massive concrete structures.

It is a more particular object of the invention to provide a method for partial heating or cooling of portions of a massive concrete structure during construction, in order to prevent formation of cracks.

SUMMARY OF THE INVENTION

The present invention overcomes the difficulties of the prior art, by providing a novel method for placing concrete in design and construction of a massive concrete structure. In accordance with the inventive method, it is possible to calculate an accurate distribution of stress that will develop in the concrete. Because accurate prediction of stress distribution is made possible, the invention thus makes it possible to use a thermal stress control technique. That is, simply by heating or cooling the concrete in the vicinity of the portion which has been predicted to become overstressed, the invention makes it possible to maintain the stress in the concrete below a maximum level (at which cracks would develop) during and after construction. This technique, for heating/cooling portion(s) of the concrete, is very effective in terms of design of massive concrete structures. Indeed, it is possible to introduce a heat pump system for the partial heating/cooling concept of the invention.

Thus the invention provides a method for placing concrete to construct a massive concrete structure, such as a dam, a bridge pier or a concrete foundation for a building, which includes: (a) determining a temperature influence function from which one can calculate a thermal stress distribution that will occur in the concrete and which will vary with temperature change; (b) predicting the location at which a crack will develop by using the temperature influence function and a function of thermal change in the concrete; (c) (partially) heating/cooling the vicinity of the predicted location and redistributing excess stress which would cause cracking in the concrete; and (d) reducing the thermal stress in the concrete by transferring the excess heat generated in the concrete structure to a desired location in the concrete which is predicted not to crack. A heat pump system should preferably be employed in implementing step (d). Further, step (a) is preferably implemented by using results of a numerical analysis rather than using the conventional concept of a constraint factor.

These and other objects, features and advantages of the present invention will become readily apparent to those skilled in the art from the following description and drawings, wherein there is shown and described a preferred embodiment of the invention, simply by way of illustration and not of limitation of one of the best modes (and alternative embodiments) suited to carry out the invention. The invention itself is set forth in the claims appended hereto. As will be realized upon examination of the specification and drawings and from practice of the same, the present invention is capable of still other, different, embodiments and its several details are capable of modifications in various obvious aspects, all without departing from the scope of the invention as recited in the claims. Accordingly, the drawings and the descriptions provided herein are to be regarded as illustrative in nature and not as restrictive of the invention.

BRIEF DESCRIPTION OF THE DRAWINGS

The accompanying drawings, incorporated into and forming a part of the specification, illustrate several aspects of a preferred embodiment of the present invention and, together with the description, serve to explain the principles of the invention. In the drawings:

FIGS. 2(a) and 2(b) show a temperature influence function used for the invention, FIG. 3 shows an influence matrix of thermal stress used for the invention, FIGS. 4(a)–4(c) show how a temperature influence function and a function of temperature change in the concrete can be used for the invention, FIGS. 5(a)–5(c) show how stress can be redistributed by partial heating in accordance with the invention.

DETAILED DESCRIPTION OF THE INVENTION

The invention will now be described in detail with reference to the drawings.

An equation for predetermining, or estimating, thermal stress by using a constraint factor is expressed in the form of $\{\sigma\}=[A]\{\Delta T\}$, where $\{\sigma\}$ represents a vector of stresses that will develop in each layer, $\{\Delta T\}$ is a corresponding vector of temperature change in each layer, and $[A]$ is an influence matrix of thermal stress. The elements $A_{ij}$ of the influence matrix describe an influence of a temperature change $\Delta T_j$, in a j-th layer of the concrete structure, to the stress $\sigma_i$ in an i-th layer of the structure. The influence matrix $[A]$ is a function both of the geometry and of the material properties of the concrete structure and the rock foundation. A numerical method, such as a finite or boundary element method, is used to specify the influence matrix.

It should be noted that, in a typical three-dimensional problem, the stress $\sigma$ is a second order symmetric tensor with 3 by 3 components, so the influence matrix may be specified in correspondence to each stress component. However, the stress component in the horizontal direction is considered to be dominant in the massive concrete problem under consideration, as such a structure has horizontal concrete layers placed on a horizontal foundation.

Figure 1:
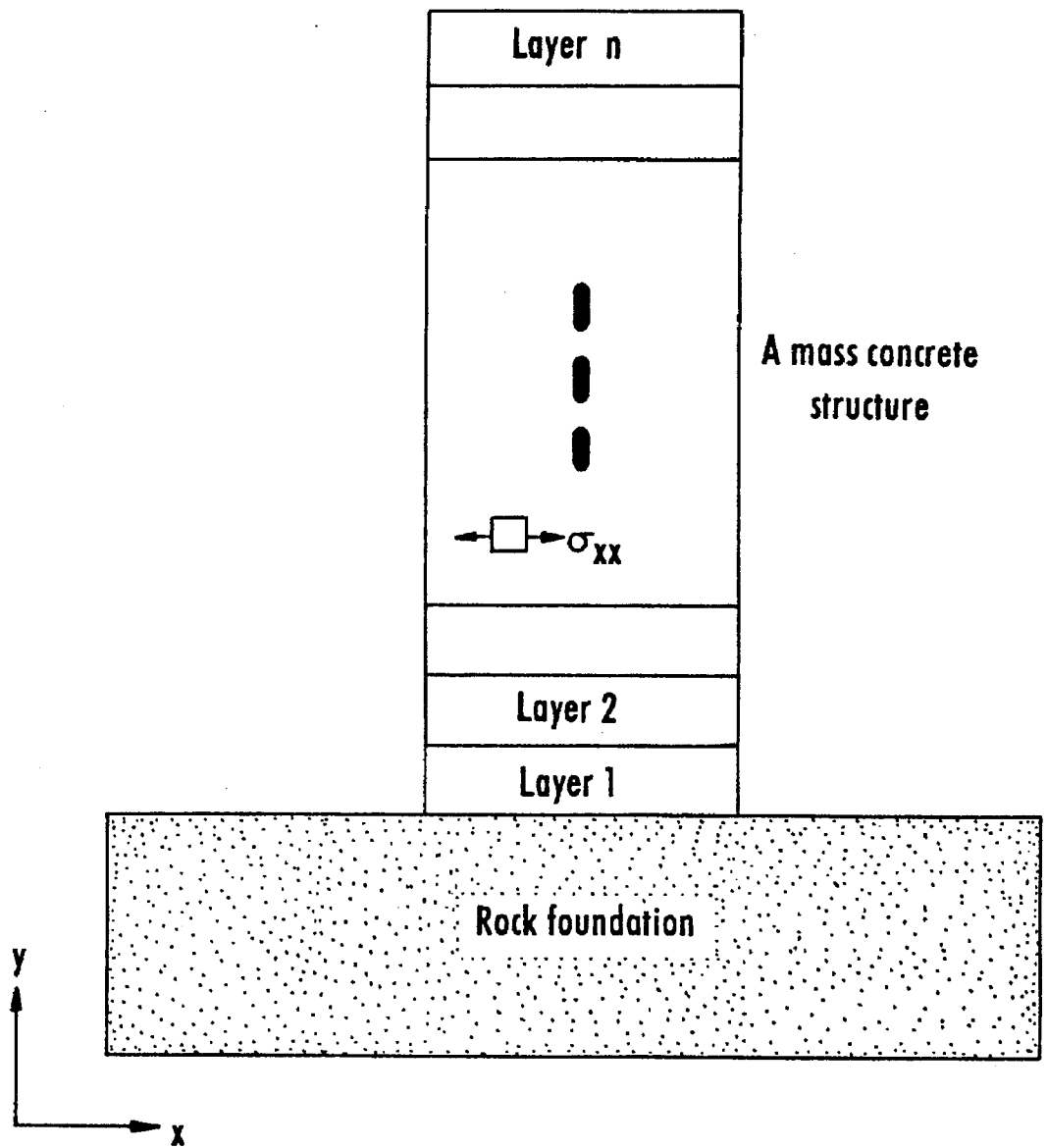
FIG. 1 shows a typical massive concrete structure having a plurality of layers.

Thus, for simplicity in illustrating the concept, one may consider only a single stress component, $\sigma_{xx}$, as shown in FIG. 1, which is designated herein as $\sigma$ for simplicity. The above influence matrix equation is developed for a concrete structure having a plurality of different layers, as hereinabove mentioned. Therein, if a temperature distribution is known for each layer, one may readily calculate the corresponding stress and check for the possibility of crack development in each layer.

The following describes how the concept of temperature influence function may be used to calculate a stress distribution in a concrete structure. Based on this concept, one can determine the characteristic profile of stress distribution in any structure. The following example provides a method for constructing a concrete structure having a rectangular shape, with a height H and a width B, placed on a horizontal rock foundation as shown in FIG. 2(a). The temperature influence function for such a structure is determined as follows.

Figure 3:
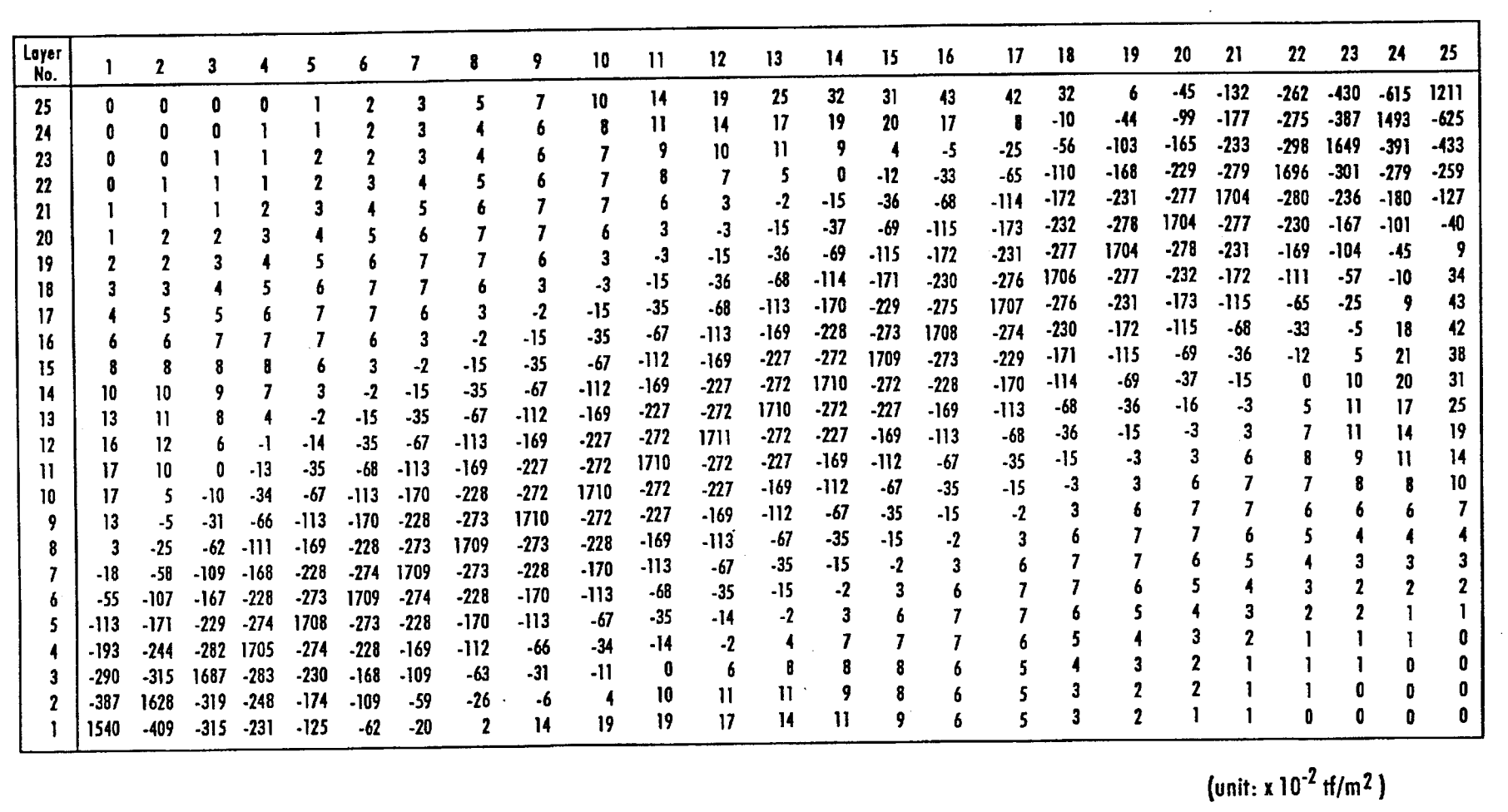

1) As shown in FIG. 2(b), an observational point (or layer at which the stress is to be calculated) may be in the bottom layer. 2) In order to calculate the stress, the values of a row of elements of the temperature influence matrix of FIG. 3, corresponding to the designated observational layer (the bottom layer), are divided by the thickness d of each layer, and then the values are plotted at each layer as shown in FIG. 2(b). 3) A function f(y), which is obtained by smoothing the plotted points as shown in FIG. 2(b), is the temperature influence function of the corresponding observational point (e.g., the bottom layer in FIG. 2(b)). It is noted that +y is the vertical upward direction.

In practice, the function f is specified as three separate parts. A first part of the function f (a function $f_1$) describes the temperature influence in an upper part of the structure, above the observational layer. A second part of the function f, a function $f_0$, shows the value of the temperature influence in the observational layer, and is in fact a constant. A third part of the function f, a function $f_2$, describes the temperature influence in a lower part of the structure, below the observational layer. The functions $f_1$ and $f_2$ may preferably be approximated in a simple form, such as a piece-wise linear or parabolic function.

If a temperature distribution in the concrete structure and in the rock foundation is given by T(y), the stress σ of the observational layer is given by the following integration $$\sigma = \int_{-\infty}^{H} T(y) f(y) \, dy.$$

Thus, if temperature influence functions of each layer can be determined by using the above procedure, the stress distribution profile may be readily determined for the entire structure.

It should be noted that the determined stress distribution is a function both of the temperature distribution T(y) and of the temperature influence function f(y). Accordingly, the inventive approach makes it possible to control excess stress by considering the configurations of either T(y) or f(y).

The following illustrates how the above theory can be applied to a practical problem in controlling an excess stress. FIG. 3 provides a temperature influence matrix of the stress σ, obtained by a finite element analysis under a plane strain condition. The conditions of the analysis are as follows. The structure is of a rectangular shape with the following dimensions:

Height H=100 [m]
Width B=50 [m] (H/B=2).
The material constants of concrete are
Elasticity modulus $E_c=2\times10^6$ [tr/m$^2$],
Poisson's ratio $\upsilon_c=0.2$, and
Thermal expansion coefficient $\alpha_c=1\times10^{-5}$ [1/° C.].
The material constants of rock foundation are
Elasticity modulus $E_r=5\times10^5$ [tf/m2],
Poisson's ratio $\upsilon_r=0.2$, and
Thermal expansion coefficient $\alpha_r=1\times10^{-5}$ [1/° C.].
The ratio of the elasticity modulus of the concrete to that of the rock foundation is $E_c/E_r=4$.

It is noted that in FIG. 3 the concrete structure is divided along horizontal lines into 25 layers, with a bottom layer numbered "1", a second layer from the bottom layer numbered "2", and so on. The topmost layer is numbered "25". The coefficients corresponding to the rock foundation are omitted from FIG. 3.

FIG. 4(a) shows a temperature influence function f(y) for the first layer, using a piece-wise linear approximation. If a periodic temperature distribution is projected to occur during a two year construction project beginning in April, a compressive stress for the first layer is obtained as σ=−52.36 [tf/m$^2$]. On the other hand, if the periodic temperature distribution of FIG. 4(c) is projected to occur during construction, corresponding to one year of construction starting in April, the stress at the first layer is calculated to be σ=−49.89 [tf/m$^2$].

It should be noted that the stress level calculated for the case of a one-year construction period is lower than the stress level obtained for a two year construction period. This surprising and unexpected result may contradict common knowledge and expectation in concrete engineering.

The following description presents a procedure for controlling thermal stress by heating. For example, during construction of the concrete structure of FIG. 1 on a horizontal rock foundation, let it be supposed that a constant temperature drop occurs at each layer. Then, the temperature profile of the structure just after completion may be represented by the thin solid line in FIG. 5(b). For purposes of illustration, the elasticity modulus and Poisson's ratio are assumed to be constant. Under these assumptions, FIG. 5(b) indicates that the peak stress is developed at a layer located at one fourth of the full height of the structure, i.e., one fourth the structure's height above the surface of the foundation rock. This peak stress may be reduced to an acceptable level by heating the concerned layer and the vicinity thereof. Thus, as shown in FIG. 5(c), additional stress can be supplied by such heating. The stress profile for the added stress is indicated by a dashed line in FIG. 5(b), and the combined stress, showing the effects of the added stress, is then reduced to a level indicated by a thick solid line of FIG. 5(b). The excess stress is now redistributed to the entire structure, so that the overall stress in the structure is reduced by the inventive method to a level below the level at which cracks might develop. It should be noted that, since the stress acting on the structure changes with time, an adequate amount of heat must be supplied at the proper time and place.

Similarly to the foregoing illustration, it is also possible to introduce a partial (local) cooling technique as required, and the procedure is entirely the same as the above-mentioned partial heating except that a negative heat supply is used (i.e., the sign of T(y) is opposite to that used for heating).

Figure 6:
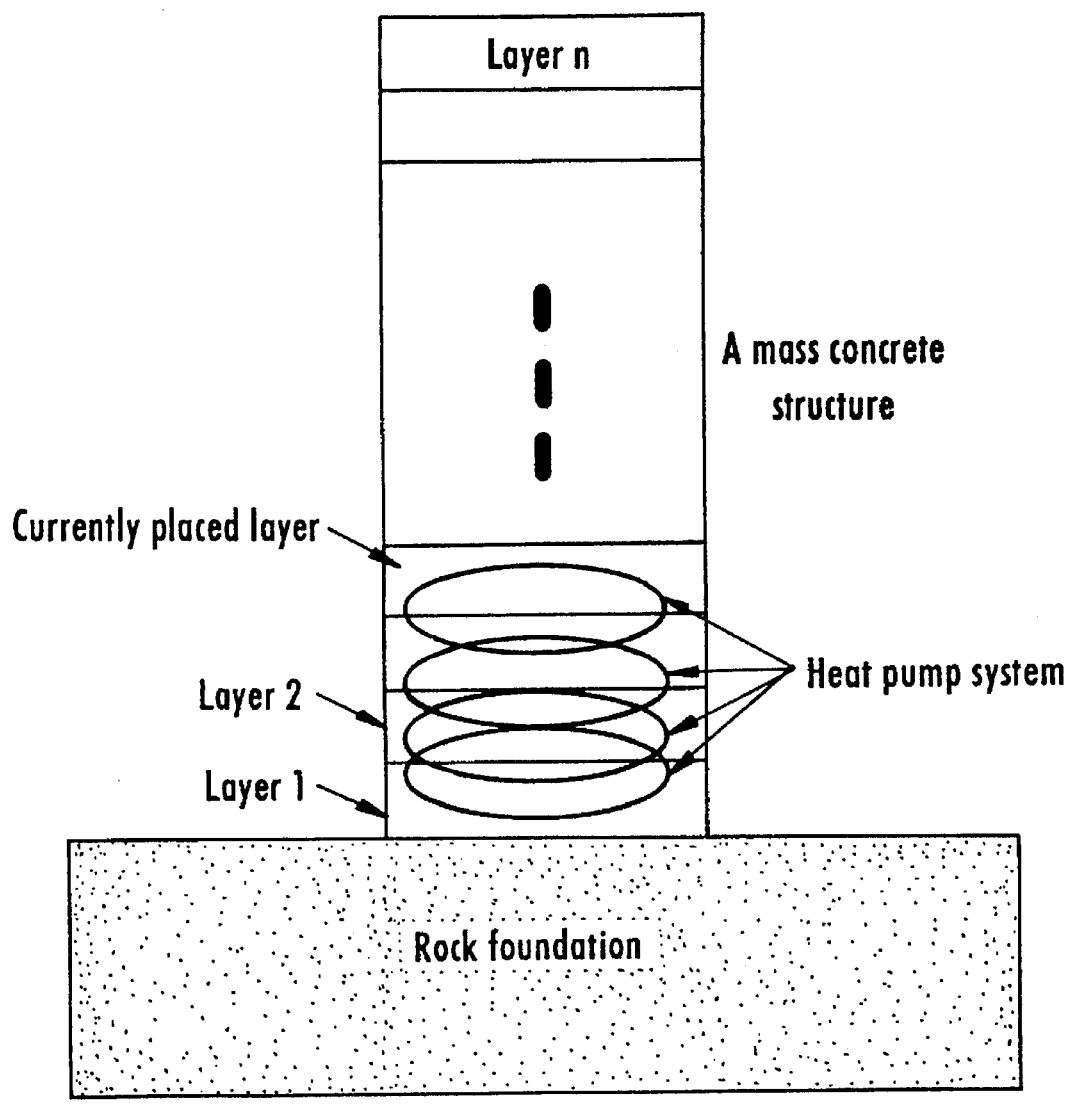
FIG. 6 shows a heat pump system that can be used to transfer excess heat generated in one portion of a concrete structure to another desired portion.

FIG. 6 represents a heat pump system for transferring excess heat generated in one portion of the concrete structure to any other desired portion of the structure, which is at a lower temperature. Such a heat pump system should preferably be used for implementing the inventive concept of partial heating/cooling.

In accepted procedures, it is expected that formation of cracks in massive concrete structures is inevitable. However, in accordance with the present invention, there has thus been disclosed a new technology of partial heating/cooling, which controls the stress generated in a massive concrete structure and thus prevents formation of cracks in the concrete. The invention thus makes it possible to safely construct a massive concrete structure such as a huge dam, a pier of a suspension bridge or a foundation of a high-rise building, without any development of cracks. Additionally, it should also be noted that in accordance with the invention a concrete structure may be constructed not only safely but also economically. This advantage results because the invention makes it possible to complete a concrete structure rapidly, with no concern for crack formation.

The foregoing description of the preferred embodiment of the invention has been presented for purposes of illustration and description. It is not intended to be exhaustive or to limit the invention to the precise forms disclosed, since many modifications or variations thereof are possible in light of the above teaching. All such modifications and variations are within the scope of the invention. The embodiments described herein were chosen and described in order best to explain the principles of the invention and its practical application, thereby to enable others skilled in the art to utilize the invention in various embodiments and with various modifications as are suited to the particular use contemplated therefor. It is intended that the scope of the invention be defined by the claims appended hereto, when interpreted in accordance with the full breadth to which they are legally and equitably entitled.

I claim:

1. A method for placing concrete on a rock foundation to construct a massive concrete structure, including the following steps for preventing concrete from being stressed beyond a predetermined stress limit for initiation and propagation of cracks therein, including:

(a) finding a temperature influence function for the concrete being placed, for enabling calculation of a thermal stress distribution in the concrete responsive to a temperature change by using results of a numerical analysis;

(b) using said temperature influence function and a function of thermal change in the structure for identifying a portion of the concrete at which a crack is predicted to develop;

(c) changing of a temperature of the identified portion and of a local vicinity thereof for redistributing an excess stress which would produce the crack in the identified portion; and (d) reducing thermal stress in the concrete by transferring an excessive amount of heat from the identified portion of the structure at which a crack is predicted to develop to a different portion thereof other than an identified portion at which a crack is predicted to develop.

2. A method in accordance with claim 1 wherein said step of reducing thermal stress comprises using a heat pump system for transferring the excessive amount of heat to the different portion of the structure thereby redistributing the excess stress to the different portion.

3. In a method for placing concrete on a rock foundation to construct a concrete structure, the improvement comprising:

preventing initiation and propagation of cracks in the concrete by preventing stress in the concrete from exceeding a predetermined stress limit, said step of preventing stress including the steps of:

(a) identifying a temperature influence function for the concrete being placed, (b) calculating a thermal stress distribution in the concrete responsive to a temperature change;

(c) using said temperature influence function and a function of thermal change in the structure for identifying a portion of the concrete at which a crack is predicted to develop;

(d) changing a temperature of the identified portion and of a local vicinity thereof for redistributing an excess stress predicted to produce the crack in the identified portion; and (e) reducing thermal stress in the concrete by transferring excess heat from the identified portion of the structure at which the crack is predicted to develop to a different portion thereof other than an identified portion at which a crack is predicted to develop.

4. In a method for placing concrete on a rock foundation to construct a multi-layer concrete structure, the improvement comprising:

preventing initiation and propagation of cracks in the concrete by preventing stress in the concrete from exceeding a predetermined stress limit, said step of preventing stress including the steps of:

(a) identifying elements $a_{ij}$ of an influence matrix describing an influence of a temperature change $\Delta T_j$, in a j-th layer of the concrete structure, to a stress $\sigma_i$ in an i-th layer of the structure;

(b) from the elements of the influence matrix, deriving a temperature influence function f(y) for the concrete being placed, describing a stress distribution in the concrete structure resulting from a temperature change;

(c) from the temperature influence function, identifying a thermal stress distribution in the concrete in accordance with a temperature distribution in the concrete structure and in the rock foundation;

(d) from the thermal Stress distribution, identifying a portion of the concrete at which a crack is predicted to develop;

(e) changing a temperature of the identified portion and of a local vicinity thereof to redistribute an excess stress predicted to produce the crack in the identified portion; and (f) reducing thermal stress in the concrete by transferring excess heat from the identified portion of the concrete structure at which the crack is predicted to develop to a different portion of the concrete structure other than an identified portion at which a crack is predicted to develop, thereby preventing the predicted crack from developing in the identified portion.

* * * * *